(12) United States Patent
Salters et al.

(10) Patent No.: US 12,037,091 B2
(45) Date of Patent: Jul. 16, 2024

(54) SYSTEM FOR ANTI-BIOFOULING

(71) Applicant: KONINKLIJKE PHILIPS N.V., Eindhoven (NL)

(72) Inventors: Bart Andre Salters, Eindhoven (NL); Roelant Boudewijn Hietbrink, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/203,698

(22) Filed: May 31, 2023

(65) Prior Publication Data

US 2023/0322340 A1 Oct. 12, 2023

Related U.S. Application Data

(63) Continuation of application No. 16/744,279, filed on Jan. 16, 2020, now abandoned, which is a continuation of application No. 15/314,961, filed as application No. PCT/EP2015/064851 on Jun. 30, 2015, now Pat. No. 10,556,651.

(30) Foreign Application Priority Data

Jun. 30, 2014 (EP) .................................. 14174966

(51) Int. Cl.
*A61L 2/10* (2006.01)
*B08B 17/02* (2006.01)
*B63B 59/04* (2006.01)

(52) U.S. Cl.
CPC ............... *B63B 59/04* (2013.01); *A61L 2/10* (2013.01); *B08B 17/02* (2013.01)

(58) Field of Classification Search
CPC .................................. A61L 2/10; B63B 59/04
See application file for complete search history.

(56) References Cited

U.S. PATENT DOCUMENTS

| 4,234,907 | A | | 11/1980 | Daniel |
| 5,308,505 | A | | 5/1994 | Titus et al. |
| 5,322,569 | A | | 6/1994 | Titus et al. |
| 5,381,506 | A | * | 1/1995 | Amick ..................... G02B 6/30 385/129 |

(Continued)

FOREIGN PATENT DOCUMENTS

| JP | 5675290 A | 6/1981 |
| JP | 11278374 A | 10/1999 |

(Continued)

*Primary Examiner* — Sean M Luck

(57) ABSTRACT

The invention provides an anti-fouling lighting system configured for preventing or reducing biofouling on a fouling surface of an object, by providing an anti-fouling light via an optical medium to said fouling surface, the anti-fouling lighting system comprising: a lighting module comprising a light source configured to generate an anti-fouling light, and said optical medium configured to receive at least part of the anti-fouling light, the optical medium comprising an emission surface configured to provide at least part of said anti-fouling light; and comprising silicone that includes particles of, for example, silica, glass, or mica, wherein a density of the particles in the silicone increases from within the optical medium towards the emission surface.

20 Claims, 4 Drawing Sheets

(56) References Cited

U.S. PATENT DOCUMENTS

| | | | |
|---|---|---|---|
| 5,905,837 A * | 5/1999 | Wang | G02B 6/2817 |
| | | | 385/127 |
| 5,952,663 A | 9/1999 | Blatchley | |
| 5,982,967 A | 11/1999 | Mathis | |
| 6,169,835 B1 | 1/2001 | Lambert | |
| 6,276,292 B1 | 8/2001 | Soulek | |
| 6,347,172 B1 | 2/2002 | Keller | |
| 6,468,433 B1 | 10/2002 | Tribelski | |
| 6,546,174 B2 | 4/2003 | Clarkin | |
| 6,742,916 B1 * | 6/2004 | Dunn | B60Q 1/32 |
| | | | 362/540 |
| 6,965,709 B1 | 11/2005 | Weiss | |
| 7,049,622 B1 | 5/2006 | Weiss | |
| 7,178,941 B2 * | 2/2007 | Roberge | H05B 45/37 |
| | | | 362/240 |
| 7,329,857 B1 | 2/2008 | Weiss | |
| 7,401,961 B2 | 7/2008 | Longatti | |
| 8,548,293 B2 | 10/2013 | Kachmar | |
| 8,620,123 B2 | 12/2013 | Dean | |
| 8,805,141 B2 * | 8/2014 | Fewkes | G02B 6/001 |
| | | | 385/100 |
| 2003/0063857 A1 | 4/2003 | Sakamoto | |
| 2004/0141420 A1 | 7/2004 | Hardage | |
| 2004/0231975 A1 | 11/2004 | Boyd et al. | |
| 2005/0175658 A1 | 8/2005 | Demauro | |
| 2006/0283786 A1 | 12/2006 | Harbers | |
| 2007/0097108 A1 | 5/2007 | Brewer | |
| 2008/0192463 A1 | 8/2008 | Fan | |
| 2008/0205892 A1 | 8/2008 | Baiden | |
| 2009/0072165 A1 | 3/2009 | Townsend | |
| 2009/0129733 A1 | 5/2009 | Keller | |
| 2009/0314193 A1 * | 12/2009 | Groves | B63B 59/04 |
| | | | 114/222 |
| 2010/0226116 A1 | 9/2010 | Brainard | |
| 2011/0019403 A1 | 1/2011 | Tsai | |
| 2011/0056276 A1 | 3/2011 | Scott | |
| 2011/0117294 A1 | 5/2011 | Nevid et al. | |
| 2011/0120956 A1 | 5/2011 | Ivanter | |
| 2011/0139729 A1 | 6/2011 | Nupnau | |
| 2011/0197919 A1 * | 8/2011 | Tilley | B08B 17/02 |
| | | | 134/9 |
| 2011/0211793 A1 | 9/2011 | Barrett | |
| 2012/0050520 A1 | 3/2012 | Thoren | |
| 2012/0211437 A1 | 8/2012 | Seaver | |
| 2013/0048877 A1 | 2/2013 | Thoren et al. | |
| 2013/0114292 A1 * | 5/2013 | Brick | G02B 6/0076 |
| | | | 362/608 |
| 2013/0202262 A1 | 8/2013 | Haymore | |
| 2014/0196745 A1 | 7/2014 | Whelan | |
| 2014/0247690 A1 * | 9/2014 | MacQuin | G01V 1/3843 |
| | | | 367/15 |

FOREIGN PATENT DOCUMENTS

| | | |
|---|---|---|
| SU | 198165 | 6/1967 |
| WO | 2007107722 A1 | 9/2007 |
| WO | 2014188347 A1 | 11/2014 |
| WO | 2016001227 A1 | 1/2016 |

* cited by examiner

SYSTEM FOR ANTI-BIOFOULING

CROSS-REFERENCE TO PRIOR APPLICATIONS

This application a continuation of U.S. application Ser. No. 16/744,279 filed Jan. 16, 2020 which is a continuation of U.S. application Ser. No. 15/314,961 filed on Nov. 30, 2016 which claims the benefit of International Application No. PCT/EP2015/064851 filed on Jun. 30, 2015, which claims the benefit of European Patent Application No. 14174966.3, filed on Jun. 30, 2014. These applications are hereby incorporated by reference herein.

FIELD OF THE INVENTION

The invention relates to an anti-fouling lighting system and to an object, such as a vessel or other (movable) construction for use in especially water, comprising such anti-fouling lighting system. The invention further relates to a method of anti-fouling a fouling surface (of such object). Further, the invention relates to a method of providing an anti-fouling lighting system to an object, such as a vessel.

BACKGROUND OF THE INVENTION

Anti-biofouling methods are known in the art. US2013/0048877, for instance, describes a system for anti-biofouling a protected surface, comprising an ultraviolet light source configured to generate ultraviolet light; and an optical medium disposed proximate to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

JPH11278374 describes that that in a dock facility, a contamination preventing means, acting statically for preventing contamination when a dock inside wall face and a hull outside face are in the atmospheric/submerged ambience, is arranged in the vicinity of the dock inside wall face. The contamination preventing means is provided with a photocatalyst reaction body arranged on the dock inside wall face and a light generating means generating either of ultraviolet or visible rays. For preventing the dock inside wall from contamination under the atmospheric ambience, it is irradiated by natural light such as sunlight or ultraviolet light from the light generating means. Then, a photocatalytic reaction is generated in the photocatalyst part carried by the photocatalyst reaction body, and an organic body as a pollutant adhering to the dock inside wall face and the photocatalyst reaction body is decomposed and purification is carried out.

U.S. Pat. No. 5,308,505 describes that biofouling of underwater surfaces by marine organisms is prevented by irradiating the water with ultraviolet light and adjusting the intensity of the ultraviolet light so as to kill barnacle larvae to prevent their attachment to the underwater surface. The water is passed through a biocidal chamber having a source of ultraviolet light at an intensity of at least 4000 mu watts/cm 2 and at a rate to provide a residence time of at least one minute on the biocidal chamber.

SUMMARY OF THE INVENTION

Biofouling or biological fouling (herein also indicated as "fouling") is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Nontoxic mechanical strategies that prevent organisms from attaching include choosing a material or coating with a slippery surface, or creation of nanoscale surface topologies similar to the skin of sharks and dolphins which only offer poor anchor points.

Biofouling on the hull of ships causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

Herewith an approach is presented based on optical methods, in particular using ultra-violet light (UV). It appears that most micro-organisms are killed, rendered inactive or unable to reproduce with 'sufficient' UV light. This effect is mainly governed by the total dose of UV light. A typical dose to kill 90% of a certain micro-organism is 10 mW-hours per square meter, details are contained in the following paragraphs regarding UV light, and the associated Figures. Prior art systems, however, may be inefficient in their use and waste a lot of radiation in the water without removing biofouling.

Hence, it is an aspect of the invention to provide an alternative anti-fouling lighting system and/or a vessel, or other object, comprising such anti-fouling lighting system and/or a (movable) construction, or other object for use in water comprising such anti-fouling lighting system and/or an alternative method of anti-fouling an element (of such vessel or constructions, or other object, etc.), which preferably further at least partly obviate one or more of above-described drawbacks.

In a first aspect, the invention provides a feedback system. The lighting system may e.g. include a sensor, which monitors relevant parameters to the occurrence of bio-fouling, thereby allowing the system to adjust the power to the light sources, such as LEDs, based on these parameters. The main advantages of reduced power are two-fold: reduced energy consumption of the system, and increased lifetime of the system. Further it appears (see also below) that in a more efficient way fouling may be removed. Parameters that appear to influence (the speed of growth of) bio-fouling are one or more of:

Speed of a vessel. Above certain speeds, bio-fouling may substantially be reduced;

Water temperature: the colder the water, the less active bio-fouling will be. Below certain temperatures, bio-fouling is negligible;

"Depth" of the boat: an empty boat will be much higher in the water. This has two effects: certain parts of the hull are now above the waterline, and will not suffer as much from fouling. The light sources, such as LEDs can be turned off here more often. Other parts will still be below the waterline, though much closer to the surface; here the intensity of sunlight is higher, promoting bio-fouling. To counter this, the power should be increased just below the waterline ("liquid level" or "water level");

"Biological activity" of the water. Obviously, in water without any bio-fouling organisms, no light source power, such as LED power is needed at all. In water with very low concentrations of algae, barnicles, etc, a lower dose of UV light will suffice to prevent bio-fouling. Monitoring these biological conditions will enable a reduced power output.

Such parameters are indicative of a biofouling risk and can be identified by one or more sensors. Such sensor(s) may provide a corresponding signal related to the bioufouling risk. Hence, the feedback signal may thus be related to a biofouling risk.

In a further aspect, which may optionally be combined with the former, the invention provides a pulsed power operation. Amongst others, a driving scheme for the light sources, such as LEDs, is proposed. Rather than a simple "24/7" on scheme, we propose to vary the power. The reason is that with 24/7 operation of the anti-bio-fouling system, a lot of energy is wasted by generating UV light that 'simply' is sent into the water surrounding the boat, without ever encountering micro-organisms. This waste of energy also implies a waste of LED lifetime. In this aspect, it is intended to generate a relatively high dose of UV, in (short) bursts. This will quickly kill (or render harmless) all micro-organisms that are close to, or attached to, the hull. After this, a predetermined amount of time, the LEDs will be switched off. During this time, algae and other organisms will accumulate on the hull. Since the entire hull is now covered, no light can 'escape' into the water without first hitting (killing) some micro-organisms.

Therefore, in a first aspect the invention provides anti-fouling lighting system ("system"), especially configured for preventing or reducing biofouling on a fouling surface of an object, that during use is at least temporarily exposed to water, by providing an anti-fouling light to said fouling surface, the anti-fouling lighting system comprising a lighting module comprising (i) a light source configured to generate said anti-fouling light, especially to prevent or to reduce biofouling on said fouling surface; and a control system configured to control an intensity of the anti-fouling light as function of one or more of (i) a feedback signal related to a biofouling risk, (ii) a timer for time-based varying the intensity of the anti-fouling light, and (iii) (an)other parameter(s) defined herein.

Hence, in a further aspect the invention provides an anti-fouling lighting system ("system") (especially configured for preventing or reducing (water related) biofouling on a fouling surface of an object, that during use is at least temporarily exposed to water (or another liquid), by providing an anti-fouling light ("light") via an optical medium to said fouling surface, the anti-fouling lighting system) comprising: (a) a lighting module ("module") comprising (i) a light source configured to generate an anti-fouling light, and (ii) said optical medium ("medium") configured to receive at least part of the anti-fouling light, the optical medium comprising an emission surface configured to provide at least part of said anti-fouling light, wherein especially the anti-fouling light comprises UV light; and (b) a control system configured to control an intensity of the anti-fouling light as function of one or more of (i) a feedback signal related to a biofouling risk and (ii) a timer for time-based varying the intensity of the anti-fouling light. In an embodiment, the timer may periodically vary the intensity of the anti-fouling light.

Especially, the invention also provides an embodiment of the anti-fouling lighting system wherein the lighting module comprises (i) the light source configured to generate the anti-fouling light and (ii) the optical medium configured to receive at least part of the anti-fouling light and configured to distribute at least part of the anti-fouling light through the optical medium, the optical medium comprising (iia) a first medium face, and (iib) an emission surface configured to emit at least part of the distributed anti-fouling light in a direction away from the first medium face of the optical medium. Such emission surface may be the fouling surface and/or the anti-fouling light may (also) be used to irradiate an(other) fouling surface.

In a specific embodiment, the invention provides an anti-fouling lighting system comprising: (a) an element, such as from an object, the element comprising a first element surface (and a second face), the first element surface especially comprising an area of at least 0.4 $m^2$; (b) a lighting module comprising (i) a light source configured to generate an anti-fouling light and (ii) an optical medium configured to receive at least part of the anti-fouling light and configured to distribute at least part of the anti-fouling light through the optical medium, the optical medium comprising (iia) a first medium face, especially having an area of at least 0.4 $m^2$, with first medium face directed to the first element surface of the element, and (iib) an emission surface configured to emit at least part of the distributed anti-fouling light in a direction away from the first medium face of the optical medium, wherein at least part of the lighting module is configured to seal at least part of the first element surface with the emission surface configured more remote from the first element surface than the first medium face; and (c) a control system configured to control an intensity of the anti-fouling light as function of one or more of a feedback signal (related to a biofouling risk) and a timer. Especially, the optical medium comprises one or more of a waveguide and an optical fiber.

Such system allows a lower power operation, which also comes with the benefit of a longer lifetime for the LED system. Further, such system allows a much more efficient removal of biofouling or prevention of biofouling. For instance, the light source may only be switched on under conditions that biofouling may be formed. Alternatively, the light source may only be switched on after e.g. a specific time in which a film of biofouling is formed, which may then efficiently be removed with the light. Hence, the system allows a higher energy efficiency and/or a better prevention and/or a more efficient removal. Herein, the term "fouling" or "biofouling" or "biological fouling" are interchangeably used. Above, some examples of fouling are provided. The described method (see below) and lighting system can be applied to prevent fouling on hulls of ships, but they are applicable to all marine objects including stationary (pipes, marine stations etc.) and/or moving marine objects (submarines etc.). The disclosed anti-fouling solution may also be applied to objects operating in waterways, canals or lakes and for example also to aquariums, etc.

In yet a further embodiment, the anti-fouling lighting system comprises an integrated unit, the integrated unit comprising (i) the lighting module and (a) one or more of a control system, a timer and a sensor, wherein the control system is configured to control an intensity of the anti-fouling light as function of one or more of (i) a feedback signal from the sensor related to a biofouling risk and (ii) a timer for time-based varying the intensity of the anti-fouling light, and the integrated unit optionally comprising also other elements, like an electrical energy source. Further, the anti-fouling lighting system may include an energy system configured to provide electrical energy to the light source (and other electric components). Sources of energy that can be used by the energy system are described below. Such units can conveniently be attached to an existing surface of an object to prevent or reduce fouling. Especially, the integrated unit is a closed unit, including the emissive surface. The integrated unit may e.g. comprise a (silicone) foil or a (silicone) tile, that may be applied to the surface of an (element of the) object. At least part of all, or even all elements, may be embedded therein. Hence, in an embodiment the optical medium comprises a foil.

In yet a further aspect, the invention also provides an object (such as e.g. selected from the group consisting of a vessel and a (movable) construction in water, that during use is at least temporarily exposed to water, the object) comprising a fouling surface that during use is at least temporarily in contact with water, the object further comprising the lighting module and the control system as defined herein, wherein the lighting module is configured to irradiate with the ant-fouling light at least part of said fouling surface. Especially, the object may further comprise the anti-fouling lighting system as described herein.

The fouling surface may be a part of the surface of (an element of) the object and/or may be the emissive surface of the lighting system (especially of the optical medium, when comprised by the lighting system; see also below). Hence, in embodiments the object is selected from the group consisting of a vessel, a weir, a dam, a stew, a sluice, a fish farming sea cage, and a buoy, etc.

In yet a further embodiment, the invention provides a vessel (as object), the vessel comprising a hull comprising an element, the element comprising a first element surface, wherein the lighting module comprises (i) the light source configured to generate the anti-fouling light and (ii) the optical medium configured to receive at least part of the anti-fouling light and configured to distribute at least part of the anti-fouling light through the optical medium, the optical medium comprising (iia) a first medium face directed to the first element surface of the element, and (iib) an emission surface configured to emit at least part of the distributed anti-fouling light in a direction away from the first medium face of the optical medium, wherein at least part of the lighting module is configured to seal at least part of the first element surface with the emission surface configured more remote from the first element surface than the first medium face, wherein especially the fouling surface comprises said emission surface and/or another surface to be protected. Hence, in a further embodiment the invention provides a vessel comprising a hull, the hull comprising an element which comprises a first element surface (and a second face), the first element surface in an embodiment comprising an area of at least $0.4$ m$^2$, the vessel further comprising the lighting module and the control system as defined herein. As indicated above, optionally the lighting module, or especially the optical medium, may seal at least part of the first element surface. The term "seal" and similar terms may especially indicate that the part that is sealed is (substantially) not accessible to a liquid, such as water, especially seawater.

The term "element" may e.g. in an embodiment refer to a plate, such as a steel plate, of the hull. However, the term "element" may also refer to the entire hull. The term "element" especially refers to the part of the hull that is at the water side, especially in case of vessel embodiments. The surface of an (element of the) object to be protected may comprise steel, but may optionally also comprise another material, such as e.g. selected from the group consisting of wood, polyester, composite, aluminum, rubber, hypalon, PVC, glass fiber, etc.

In yet another aspect, the invention also provides a movable construction comprising a movable part, the movable part comprising an element which comprises a first surface (and a second face), the first surface in an embodiment comprising an area of at least $0.4$ m$^2$, the vessel further comprising the lighting module and the control system as defined herein. The movable construction may e.g. be a weir, a dam, a sluice, etc., which may have a movable part, such as a door or a valve, etc. Hence, especially the movable construction is an aquatic movable construction. The movable part may comprise an element, like a plate, such as a steel plate. Again, the term "element" may also refer to the entire movable part.

Hence, in a specific embodiment the invention also provides an embodiment of the anti-fouling lighting system, wherein the element is part of the hull of a vessel or part of the movable part of a movable construction in water, wherein the first element surface of the element especially has an area of at least $4$ m$^2$, wherein the anti-fouling lighting system comprises a plurality of lighting modules associated with the first element surface, wherein the anti-fouling lighting system comprises one or more control systems configured to control intensity of the anti-fouling light of the plurality of lighting modules as function of one or more of a feedback signal and a timer.

The element comprises a first element surface ((and a second face) and the first element surface) especially comprises an area (or "surface area") of at least $0.4$ m$^2$. The second face may e.g. be the internal face of the hull of a vessel. The first element surface will in general be in contact with a liquid, such as water (see however also below). The element will in general have a surface area of at least $0.4$ m$^2$, though it may be much larger such as at least $4$ m$^2$, like at least $400$ m$^2$, or even over $1000$ m$^2$. Further, the term element may also refer to a plurality of elements. For instance, the hull of boat may include a plurality of (metal) plates. Assuming (metal) plates as elements, the surface area may e.g. be in the range of $0.4$-$40$ m$^2$, like $2$-$10$ m$^2$.

On such surface, biofouling may occur when the element is in, or near water, such as (just) above the water level (like e.g. due to splashing water, such as for instance due to a bow wave). Between the tropics, biofouling may occur within hours. Even at moderate temperatures, the first (stages of) fouling will occur within hours; as a first (molecular) level of sugars and bacteria. With the present invention, at least part of the lighting module, such as at least part of the optical medium, or even the entire optical medium, may in embodiments seal of part of the first element surface of the element (making that part not accessible to water, such as seawater). Hence, the lighting module may in embodiments be associated with the first element surface. This, however, translates the biofouling problem to the surface(s) of the lighting module. The surface or area on which fouling may be generated is herein indicated as fouling surface. It may e.g. be the hull of a ship and/or an emission surface of an optical medium (see also below). To this end, the lighting module provides anti-fouling light that is applied to prevent formation of biofouling and/or to remove biofouling. This anti-fouling light may at least comprises UV radiation (also indicated as "UV light"). In fact, the emission surface now provides part of the external surface of the element, such as a hull.

In yet a further aspect, the invention provides a lighting module comprising (i) a light source configured to generate an anti-fouling light and (ii) an optical medium configured to receive at least part of the anti-fouling light and configured to distribute at least part of the anti-fouling light through the optical medium, the optical medium comprising (iia) a first medium face, especially having an area of at least 0.4 m$^2$, and (iib) an emission surface configured to emit at least part of the distributed anti-fouling light in a direction away from the first first medium face of the optical medium.

Especially, the invention provides an embodiment of the anti-fouling lighting system as defined herein, wherein the control system is configured to control the intensity of the anti-fouling light as function of (one or more of (a) the timer and (b)) the feedback of a sensor, wherein the sensor is configured to sense one or more of (i) a velocity of a vessel comprising said lighting module, (ii) a relative velocity of flow of water (at a side of the fouling surface), (iii) a water temperature of water (at a side of the fouling surface), (iv) a loading of a vessel comprising said lighting module, (v) a position of the emission surface relative to a water level of water (at a side of the fouling surface), and (vi) a presence of one or more of a fouling organism and a fouling organism nutrient in water (at a side of the fouling surface). Even more especially, the invention provides an embodiment of the anti-fouling lighting system as defined herein, the anti-fouling lighting system comprising: (a) a lighting module comprising (ai) a light source configured to generate an anti-fouling light and (aii) an optical medium configured to receive at least part of the anti-fouling light and configured to distribute at least part of the anti-fouling light through the optical medium, the optical medium comprising (aiia) a first medium face, especially having an area of at least 0.4 m$^2$, and (aiib) an emission surface configured to emit at least part of the distributed anti-fouling light in a direction away from the first medium face of the optical medium; (b) a sensor; and (c) a control system configured to control an intensity of the anti-fouling light as function of one or more of a feedback signal and a timer, wherein the control system is configured to control the intensity of the anti-fouling light as function of the feedback of the sensor, wherein the sensor is configured to sense one or more of (i) a velocity of a vessel comprising said lighting module, (ii) a relative velocity of flow of water (at a side of the fouling surface), (iii) a water temperature of water (at a side of the fouling surface) of said optical medium, (iv) a loading of a vessel comprising said lighting module, (v) a position of the fouling surface relative to a water level of water (at a side of the fouling surface), (vi) a presence of one or more of a fouling organism and a fouling organism nutrient in water (at a side of the fouling surface); and wherein the anti-fouling light comprises in a specific embodiment UV-C light. Alternatively or additionally, the control system may be configured to control an intensity of the anti-fouling light as function of a UV(C) transmission of the water (adjacent to the fouling surface).

Ultraviolet (UV) is that part of electromagnetic light bounded by the lower wavelength extreme of the visible spectrum and the X-ray radiation band. The spectral range of UV light is, by definition between about 100 and 400 nm (1 nm=10-9 m) and is invisible to human eyes. Using the CIE classification the UV spectrum is subdivided into three bands: UVA (long-wave) from 315 to 400 nm; UVB (medium-wave) from 280 to 315 nm; and UVC (short-wave) from 100 to 280 nm.

In reality many photobiologists often speak of skin effects resulting from UV exposure as the weighted effect of wavelength above and below 320 nm, hence offering an alternative definition.

A strong germicidal effect is provided by the light in the short-wave UVC band. In addition erythema (reddening of the skin) and conjunctivitis (inflammation of the mucous membranes of the eye) can also be caused by this form of light. Because of this, when germicidal UV-light lamps are used, it is important to design systems to exclude UVC leakage and so avoid these effects. In case of immersed light sources, absorption of UV light by water may be strong enough that UVC leaking is no problem for humans above the liquid surface. Further, especially the anti-fouling light comprises one or more of UV-A and UV-C light. Hence, in an embodiment the anti-fouling light comprises UV-C light. UV-A may be used to impair cell walls, whereas UV-C may be used to impair DNA.

Self evidently, people should avoid exposure to UVC. Fortunately this is relatively simple, because it is absorbed by most products, and even standard flat glass absorbs substantially all UVC. Exceptions are e.g. quartz and PTFE (Poly tetrafluor eth(yl)ene). Again fortuitously, UVC is mostly absorbed by dead skin, so erythema can be limited. In addition UVC does not penetrate the eye's lens; nevertheless, conjunctivitis can occur and though temporary, it is extremely painful; the same is true of erythemal effects.

Where exposure to UVC light occurs, care should be taken not to exceed the threshold level norm. In practical terms, Table 1 gives the American Congress of Governmental and Industrial Hygienist's (ACGIH) UV Threshold Limit Effective Irradiance Values for human exposure related to time. At this time it is worth noting that radiation wavelengths below 240 nm forms ozone, $O_3$, from oxygen in air. Ozone is toxic and highly reactive; hence precautions have to be taken to avoid exposure to humans and certain materials.

TABLE 1

| permissible UVC exposures for humans according to ACGIH | |
|---|---|
| Duration of exposure per day | Irradiance ($\mu W/cm^2$) |
| 8 hours | 0.2 |
| 4 hours | 0.4 |
| 2 hours | 0.8 |
| 1 hour | 1.7 |
| 30 minutes | 3.3 |
| 15 minutes | 6.6 |
| 10 minutes | 10 |
| 5 minutes | 20 |
| 1 minute | 100 |

The germicidal doses listed above can also easily be achieved with existing low cost, lower power UV LEDs. LEDs can generally be included in relatively smaller packages and consume less power than other types of light sources. LEDs can be manufactured to emit (UV) light of various desired wavelengths and their operating parameters, most notably the output power, can be controlled to a high degree. Hence, especially the light source is a light source that during operation emits (light source light) at least light at a wavelength selected from the UV wavelength range, especially at least UV-C. In a specific embodiment, the light source comprises a solid state LED light source (such as a LED or laser diode). The term "light source" may also relate to a plurality of light sources, such as 2-20 (solid state) LED light sources, though many more light sources may also be applied. Hence, the term LED may also refer to a plurality of LEDs. The LEDs may be OLEDs or solid state LEDs, or a combination of these LEDs. Especially, the light source comprises solid state LEDs.

An basic idea underlying the present disclosure is to cover significant amounts of a protected surface to be kept clean from fouling, preferably the entire protected surface, e.g. the hull of a ship, with a layer that emits germicidal light ("anti-fouling light"), in particular UV light.

In yet another embodiment, the anti-fouling light may be provided to the surface to be protected via a fiber or waveguide. Hence, in an embodiment the anti-fouling lighting system comprises an optical medium, wherein the optical medium comprises one or more of a waveguide and an optical fiber configured to provide said anti-fouling light to the fouling surface. The surface of the fiber or waveguide from which the anti-fouling light escapes is herein also indicated as emission surface. In general, this part of the fiber or waveguide may at least temporarily be submerged. Due to the anti-fouling light escaping from the emission surface, an element of the object that is during use at least temporarily exposed to the liquid (such as seawater), may be irradiated, and thereby anti-fouled. However, the emission surface per se may also be anti-fouled. This effect is used in the embodiments of the lighting module comprising an optical medium described below.

The lighting module for anti-fouling of a protected surface comprises at least one light source for generating anti-fouling light and optionally an optical medium for distributing the anti-fouling light from the light source. The at least one light source and/or the optical medium may be at least partly arranged in, on and/or near the protected surface so as to emit the anti-fouling light in a direction away from the protected surface. The lighting module is adapted to preferably emit the anti-fouling light while the protected surface is at least partially submersed in an liquid environment. In an embodiment, the optical medium is a light guide comprising a silicone material and/or UV grade silica material.

The lighting module for anti-fouling of a protected surface may also be provided as a (silicone) foil for applying to the protected surface, the foil comprising at least one light source for generating anti-fouling light and a sheet-like optical medium for distributing the anti-fouling light across the foil. In embodiments the foil has a thickness in an order of magnitude of a couple of millimeters to a few centimeters, such as 0.1-5 cm, like 0.2-2 cm. In embodiments, the foil is not substantially limited in any direction perpendicular to the thickness direction so as to provide substantially large foil having sizes in the order of magnitude of tens or hundreds of square meters. The foil may be substantially size-limited in two orthogonal directions perpendicular to the thickness direction of the foil, so as to provide an anti-fouling tile; in another embodiment the foil is substantially size-limited in only one one direction perpendicular to a thickness direction of the foil, so as to provide an elongated strip of anti-fouling foil. Hence, the optical medium, and even also the lighting module, may be provided as tile or as strip. The tile or strip may comprise a (silicone) foil.

The lighting module, whether arranged in, on and/or near the protected surface or whether provided as a separate foil, comprises an emission surface for emitting the anti-fouling light from the optical medium into an environment and a application surface, opposed the emission surface, for applying or arranging the lighting module to the protected surface. In a preferred embodiment the emission surface of the light module is substantially planar so as to avoid pits and indents which may become seeds of fouling and so as to avoid bulges to limit the amount of drag caused by the structure when applied to the protected surface. The advantage of a substantially planar surface versus a surface comprising indents and bulges or having a substantial surface roughness is that it will be more difficult for microorganisms to adhere to a substantial plane surface, especially in combination with drag effects in a liquid environment, than they would onto a rough surface or into pits comprises in said surface. The term 'substantially planar' emission surface herein refers to a surface masking or obscuring the thickness of light sources and wiring connections embed in or attached to the lighting module. The term 'substantially planar' may also refer to masking or obscuring some constructional unevenness of the protected surface, thereby even improving the drag properties of the protected surface in the liquid environment. Example of constructional unevenness of the protected surface are welds, rivets, etc. The term 'substantially planar' can be quantified as resulting in variations in the average thickness of the light modules of less than 25%, preferably less than 10%. 'Substantially planar' therefore not necessarily requires a surface roughness of a machined surface finish.

In a preferred embodiment the lighting module comprises a two-dimensional grid of light sources for generating anti-fouling light and the optical medium is arranged to distribute at least part of the anti-fouling light from the two-dimensional grid of light sources across the optical medium so as to provide a two-dimensional distribution of anti-fouling light exiting the light emitting surface of the light module. The two-dimensional grid of light sources may be arranged in a chickenwire structure, a close-packed structure, a rows/columns structure, or any other suitable regular or irregular structure. The physical distance between neighboring light sources in the grid may be fixed across the grid or may vary, for example as a function of light output power required to provide the anit-fouling effect or as function of the location of the lighting module on the protected surface (e.g location on the hull of a ship). Advantages of providing a two-dimensional grid of light sources include that the anti-fouling light may be generated close to the areas to be protected with anti-fouling light illumination, and that it reduced losses in the optical medium or light guide and that is increasing homogeneity of the light distribution. Preferably, the anti-fouling light is generally homogeneously distributed across the emission surface; this reduces or even prevents under-illuminated areas, where fouling may otherwise take place, while at the same time reducing or preventing energy waste by over-illumination of other areas with more light than needed for anti-fouling. In an embodiment, the grid is comprised in the optical medium. In yet an embodiment, the grid may be comprised by a (silicone) foil.

In preferred embodiments, the light sources are UV LEDs. The at least one UV LED or the grid of UV LEDs may be encapsulated in a liquid-tight encapsulation. In embodiments the at least one UV LED or the grid of UV LEDs may be embedded in the optical medium. A plurality of UV LEDs may be organised in grid and electrically connected in a series/parallel chicken-wire structure (as will be explained later). The LEDs and the chicken-wire connections may be encapsulated in a light-transmissive coating and attached to the optical medium or directly embed in the optical medium. In other embodiments the grid of UV LEDs may be comprised in a layer of electronic textile which is embedded in a resin structure. In some embodiments the UV LEDs may be packaged LEDs, in which case they already may include an optical element to distribute the light emitted from the LED package across a wide emission angle. In other embodiment the UV LEDs may be LED dies, typically not comprising optical elements but being significantly thinner than packaged LEDs. As an example, LED dies could be picked and placed onto a surface of the optical medium (preferably the application surface, but the emission surface would do as well because of the small size of the components which will nearly not interfering with the light emission function of said surface), electrical wired via printing of conductive paste and finally the LED dies and wiring could be encapsulated with a thin layer/coating of the optical medium or any other backing layer for applying the lighting module to the protected surface. Various embodiments of embedded light sources allow the presented anti-fouling technology to be commercialized as a foil for applying on the hull of ships.

A system for anti-fouling of a protected surface may comprise a plurality of lighting modules as disclosed herein for arranging on the protected surface so as to provide anti-fouling light over substantially the entire area of the protected surface.

Silicone materials can provide optical transmission for UV light with little loss compared to other materials. This is in particular the case for shorter wavelength light, e.g. UV light with wavelengths below 300 nm. A particularly efficient group of silicone materials is, or at least comprises, so-called methyl silicones, according to the general chemical formula $CH_3[Si(CH_3)_2O]_nSi(CH_3)_3$, with "n" indicating any suitable integral, as customary in organic chemistry. This type of silicone materials happens to exhibit excellent UV transmission properties with little losses, at least compared to other silicone materials. Further, silicone materials are flexible and resilient so that they are robust, durable and capable of withstanding compression such as due to bumps, collisions etc of objects against the surface, e.g. bumping of a ship against a quai. Instead of methyl groups also phenyl groups, or phenyl and methyl groups may be present in the silicone.

Further, deformation of a ship's skin due to temperature fluctuation, pounding by waves, ship's flexion over swell and heave etc may be accommodated. Also, silicone materials can be applied and formed over surface structures: welds, rivets, etc. in or on the surface. Silicone materials also tend to adhere well to metals and paints so that a protective coating over the surface is formed. Visibly transparent silicone materials enable reading of underlaying markings (e.g. painted symbols) covered by the silicone material. Further, they are generally water repellent and may reduce friction and drag. On the one hand silicones can be made very smooth to reduce adherence of biofouling organisms to the layer and to reduce friction against flowing water, while on the other hand the material may be finely structured so as to mimic shark's skin which is also known to reduce friction in water at sufficient speed relative to the surrounding water. It is noted that a structured surface of an optical medium, in particular a light guide, can cause breaking conditions for total internal reflection and therewith cause coupling out of light from the light guide that was otherwise captured within and transmitted with total internal reflection. Thus, coupling out of light can be localised reliably.

UV grade silica has very low absorption for UV light and thus is very well suitable as optical medium and light guide material. Relatively large objects may be made from using plural relatively small pieces or portions of UV grade silica together and/or so-called "fused silica", while retaining the UV-transmissive properties also for the larger object. Silica portions embedded in silicone material protect the silica material. In such combination the silica portions may provide UV transparent scatterers in an otherwise silicone material optical medium for (re-)distribution of the light trough the optical medium and/or for facilitating outcoupling of the light from a light guide. Also, silica particles and/or particles of other hard, UV translucent material may fortify the silicone material. In particular flake-shaped silica particles may be used, also in high density, of up to 50%, 70% or even higher percentages of silica in silicone material may provides a strong layer that can resist impacts. It is considered that at least a part of the optical medium or light guide may be provided with a spatially varying density of UV grade silica particles, in particular flakes, at least partly embedded in a silicone material, e.g. to vary optical and/or structural properties. Here, "flakes" denote objects having sizes in three cartesian directions, wherein two of the three sizes may mutually differ, however, each being significantly larger, e.g. a factor 10, 20, or significantly more, e.g. factors of 100's, than the third size.

In embodiments, in parts of the optical medium close to the emission surface for emitting the anti-fouling light from the optical medium, the density of the UV grade silica particles in the silicone material may increase from within the optical medium towards the emission surface of the optical medium, so that at or near the emission surface a relatively high density of silica particles is provided. Although more or less spherical and/or random-shaped particles may be used, silica flakes of sub-millimeter length scales, e.g. with typical sizes down to a few micrometers, may be arranged so close together that under the influence of very local forces, such as a point-impacts from sharp-tipped objects, and/or localised impacts from blunt objects, including scratches, tears etc, the flakes may have some, if only little, freedom of movement in the flexible silicone that they can slightly rearrange themselves, dissipating the impact energy and reducing damage to the light guide as a whole. Thus, a balance of properties can be struck that results in both a robust and a somewhat deformable layer, yet also providing the desired optical qualities. In an embodiment the proportion of silicone material in the optical medium varies gradually from about 100% (i.e. substantially pure silicone material) to below about 5% (mostly silica) from one side of the optical medium to an opposite side.

It is noted that particles, in particular flake-shaped particles, of other material than silica may be used, e.g. glass or mica. Such other materials may also serve as scatterers for the anti-fouling light. Mixtures of particles of different materials may also be provided, which may comprise mixtures of translucent, opaque and/or optically active particles. Compositions of such mixtures may vary across the light guide, e.g. to adjust transmittivity of the light guide for the anti-fouling light, in particular if in some portions relatively large amounts of poorly-transmitting particles are used.

For manufacturing the optical medium, a series of layers of silicone material may be formed, each possibly having a different composition with regard to the amount and/or density of silica particles. The layers may be very thin and at least some may be applied with a wet-on-wet technique, i.e. providing the silicone material to the layer in liquid or gelatinous form that should harden to the desired layer, but wherein a subsequent layer is applied to an earlier layer before the earlier layer has fully hardened. Thus, a good adhesion between the layers is promoted and in the final product different layers may be hardly to not discernible and a gradual change in composition may be achieved. Different layers may suitably be formed and/or applied by spraying of the layer material. A layered material may be formed to any suitable thickness with good quality control. Note that the optical medium, which constitutes a substantial part of the lighting module's surface, may be attached to the protected surface in any suitable way, including gluing. Silicone materials tend to exhibit strong adhesion to ceramic, glassy and metallic materials and spraying or smearing silicone material is therefore a very suitable manner of forming and attaching the optical medium to a substrate. A sprayed and/or smeared optical medium can also readily be made in different desired shapes, e.g. following a water line, specific markings and/or surface shapes. A layering technique may also facilitate orienting particles in the silicone material, e.g. arranging flakes generally parallel to the direction of expansion of the layer and the surface coated with the layer.

In another aspect of the lighting module, the optical medium comprises spaces, e.g. channels which are filled with gas and/or clear liquid, e.g. water, for guiding the light therethrough and an associated method comprises distributing at least part of the light through such spaces in an optical medium. It is found that optical transmission for UV light through gaseous matter, in particular air, is generally significantly better than transmission of the light through a solid material which may, even if found translucent or transparent by some, exhibit absorption losses of up to several percents per millimeter. Clear liquid provides little scattering, may well transport UV light and may also provide structural robustness of cavities in the optical medium compared to filling the spaces with gas. Water, most notably fresh water, has been found to have a relatively high and suitable UV transmittivity. Contamination and/or UV absorption may be also and/or further reduced if distilled, deionised and/or otherwise purified water is used. Hence, it is considered particularly beneficial to transmit the light through a gas- and/or liquid-filled space. For distribution of the light across the protected surface, the gas- and/or liquid-filled space should preferably be well defined and channels may be provided in a optical medium. Light that eventually strikes walls of the channels can enter the optical medium and be emitted from the optical medium in a direction from the protected surface and into the liquid environment to provide the anti-fouling light. An optical medium in which the air channels are defined that is itself well transparent to the anti-fouling light further assures that if the optical medium would leak and the liquid medium enters the optical medium, generated anti-fouling light would still be appropriately transmitted through the optical medium. Channels may comprise varying diameter. Localised channel portions or pockets may be provided by wall portions defining and encapsulating separate volumes (much) bigger than the respective wall portions' sizes and/or thicknesses, e.g. similar to the packaging product sold under the brand name "Bubble Wrap".

In a particular embodiment, such gas-containing optical medium comprises a silicone material defining the gas and/or liquid-filled channels and/or other spaces; silicone materials may well be shaped to define intricate structures. Further advantages of silicone materials, with or without additional objects such as silica particles have been set out above.

In an embodiment, the channels and/or other spaces are provided by forming two opposing layers of silicone material kept separated at desired distances with wall portions and/or pillars of silicone material creating a distance, e.g. an air gap between the layers. Such wall portions and/or pillars may serve as scattering centres for (re-)distributing the light through (the channels in) the optical medium and/or for guiding light from the gas-and/or liquid filled space(s) into the silicone material. This facilitates localising emission of the light from the optical medium into the liquid environment where the anti-fouling light is to be put to use.

At least part of the anti-fouling light emitted by the one or more light sources may be spread in a direction having a component substantially parallel to the protected surface, or substantially parallel to the application surface of the foil when the light moulded is provided as a foil. This facilitates distributing the light over significant distances along the protected surface, or the application surface of the foil, which assists in obtaining a suitable intensity distribution of the anti-fouling light.

A wavelength conversion material may be comprised in the optical medium and at least part of the anti-fouling light may be generated by photo-exciting the wavelength conversion material with light having a first wavelength causing the wavelength conversion material to emit the anti-fouling light at another wavelength. The wavelength conversion material may be provided as an upconversion phosphor, quantum dots, nonlinear media such as one or more photonic crystal fibers etc. Since absorption and/or scattering losses in the optical medium for light of different, mostly longer, wavelengths than UV light tend to be less pronounced in optical media, it may be more energy-efficient to generate non-UV light and transmit that through the optical medium and to generate UV anti-fouling light at or near the desired location of use thereof (i.e. emission form the surface into the liquid environment). Suitable anti-fouling light is in the wavelength range of UV or optionally also blue light from about 220 nm to about 420 nm, in particular at wavelengths shorter than about 300 nm, e.g. from about 240 nm to about 280 nm.

When a wavelength conversion material is applied, the phrase "a light source configured to generate an anti-fouling light" may be interpreted as a light source for generating in combination with a wavelength conversion material an anti-fouling light. Either the light source itself, or the wavelength conversion material upon conversion of the light source light into wavelength conversion material light, or both, provide said anti-fouling light.

In embodiments, the optical medium comprises a light spreader arranged in front of the at least one light source for generating anti-fouling light for spreading at least part of the anti-fouling light emitted by the at least one light source in a direction having a component substantially parallel to the protected surface. An example of a light spreader may be a 'opposite' cone arranged in the optical medium and position opposite the at least one light source, where the opposite cone has a surface area with a 45° angle perpendicular to the protected surface for reflecting light emitted by the light source perpendicular to said surface in an a direction substantially parallel to said surface. In embodiments the optical medium comprises a light guide arranged in front of the at least one light source for generating the anti-fouling light, the light guide having a light coupling-in surface for coupling in the anti-fouling light from the at least one light source and a light coupling-out surface for coupling-out the anti-fouling light in a direction away from the protected surface; the light guide comprising a light guide material having a refractive index higher than the refractive index of the liquid environment such that at least part of the anti-fouling light is propagated through the light guide via total internal reflection in a direction substantially parallel to the protected surface before being out-coupled at the out-coupling surface. Some embodiment may comprise an optical medium which combines a light spreader and a light guide, or integrated light spreading features with light guiding features into the optical medium. In embodiments, the light spreader and/or light guide is coated onto the protected surface. In other embodiments, the light spreader and/or light guide is provided in the form factor of a foil for applying onto a protected surface.

An embodiment of a system for preventing fouling may comprise:
  a series of UV LEDs for generating anti-fouling light;
  a light spreader for spreading the anti-fouling light from the LED point sources across the protected surface; and
  a light guide (or waveguide) for further guiding/spreading the anti-fouling light can be spread across the surface, the light guide comprising a tin layer of silicone material transparent to UV light, with or without silica particles or one or more silica covered portions.

When substantially the entire protected surface is covered with an anti-fouling light emitting optical medium, it substantially reduces the growth of micro-organisms on this medium. As the micro-organisms are killed on the emission surface of the optical medium, the hull is continuously cleaned through the water flow along the hull which transports the debris away from the ship and micro-organisms do not stand a chance of fouling on the hull.

It is an advantage of the presently provided solutions that the micro-organisms are not killed after having adhered and rooted on the fouling surface, as is the case for known poison dispersing coatings, but that the rooting of micro-organisms on the fouling surface is prevented. It is more efficient to actively kill micro-organism right before or just after they contact the fouling surface, compared to a light treatment to remove existing fouling with large micro-organism structures. The effect may be similar to the effect created by using nano-surfaces that are that smooth that micro-organism cannot adhere to it.

Because the low amount of light energy required for killing the micro-organism in the initial rooting stage, the system may be operated to continuously provide an anti-fouling light across a large surface without extreme power requirements.

A grid of LEDs creating a lighting surface may be provided with energy harvesting means such as for example embedded solar cells, small turbines operating in the water, piezoelectric elements operating on pressure waves, etc. To this end, the lighting system may also include an energy system for providing energy to the light source and other electric components.

Some advantages of the presently provided technology include the retention of clean surface, reduction of the cost of corrosion treatment, reduced fuel consumption for ships, reduced maintenance time for hulls, reduced $CO_2$ emission, reduced use of toxic substances in the environment, etc. A substantially planar and smooth light emission surface further has the advantage of not adding drag by itself and can even further reducing drag by burying existing unevenness (rivets, welds, etc.) of the protected surface underneath the optical medium.

The object (see also below) may comprise one or more elements that are at least temporarily exposed to the liquid. Such element may include a first element surface, which may at least temporarily be exposed to the liquid. Such element may also comprise a second element surface, which may be directed to the body of the object.

Instead or in addition to silicone, as material for the optical medium, one or more materials selected from the group consisting of a transmissive organic material, such as selected from the group consisting of PE (polyethylene), PP (polypropylene), PEN (polyethylene napthalate), PC (polycarbonate), polymethylacrylate (PMA), polymethylmethacrylate (PMMA) (Plexiglas or Perspex), cellulose acetate butyrate (CAB), polyvinylchloride (PVC), polyethylene terephthalate (PET), (PETG) (glycol modified polyethylene terephthalate), PDMS (polydimethylsiloxane), and COC (cyclo olefin copolymer) may be applied. Especially, the optical medium is not stiff. For instance, the optical medium may be applied to a hull of a ship. However, the optical medium may also be constructed on the hull of a ship by coating material to the hull and thereby forming the optical medium.

The optical medium is configured to receive at least part of the anti-fouling light of the light source. Hence, especially the light source and the optical medium are radiationally coupled. The term "radiationally coupled" especially means that the light source and the optical medium are associated with each other such that at least part of the radiation emitted by the light source is received by the optical medium. The optical medium is configured to distribute the anti-fouling light through the optical medium. This may be due to the fact that the optical medium especially has lightguiding (of waveguiding) properties. Optionally, the light source is embedded in the optical medium (see also below).

Further, the optical medium may also include outcoupling structures to couple the anti-fouling light out. Hence, anti-fouling light that may be captured within the optical medium by total internal reflection may escape due to outcoupling via an outcoupling structure. These outcoupling structures may be embedded in the optical medium and/or may be configured at a surface of the optical medium. Especially, the outcoupling structures, optionally in combination with a reflector at at least part of the first medium face, are configured to facilitate emission of the anti-fouling light from the emission surface, in a direction away from the first medium face (i.e. during use of the lighting module: away from the first element surface of the element). This light is used to prevent biofouling and/or remove biofouling at the emission surface of the lighting module.

As indicated above and below, the lighting module may essentially consist of the optical medium. For instance, one or more of the control system and a power supply may be embedded in the optical medium. Further, as a single LED may provide anti-fouling light through a large area of the optical medium, in an embodiment the surface area of the lighting module may consist for at least 80% of the optical medium. The optical medium may be used to seal the element. Hence, the first medium face may have a surface area substantially equal to the surface area of the first element surface, though it may also be smaller when a plurality of optical media is applied (see also below).

Especially, the first medium face is in physical contact with the first element surface. Even more especially, the entire first medium face is in physical contact with the first element surface. The phrase "with the emission surface configured more remote from the first element surface than the first medium face", indicates that the first medium face of the optical medium is closer to the first element surface of the element than the emission surface. In this way, anti-fouling light may escape in in a direction away from the element. As indicated above, in some embodiment at least part of the first medium face, or especially the entire first medium face, may be in physical contact with the (first element surface of the) element.

More than one lighting module may be applied to a single element. Hence, the term "lighting module" may also refer to a plurality of lighting modules. Further, a single lighting system may include a plurality of optical mediums. Hence, the term "optical medium" may also refer to a plurality of optical mediums. Of course, the anti-fouling lighting system may also include a plurality of elements. Hence, as indicated above, the term "element" may also refer to a plurality of lighting elements.

In an embodiment, the lighting module comprises said control system and optionally also a power supply. In this way, a system may be provided at the first element surface of the element, without the necessity to include through holes through the element. This may be beneficial, amongst others in view of protection of the element. Further, the power supply may optionally include a local energy harvesting system, such as a system that generates electrical energy from water, especially seawater, and/or a photovoltaic system. Both may advantageously be arranged at such element, with the former especially below the (expected) water level and the latter especially above the (expected) water level.

As indicated above, the control system is configured to control an intensity of the anti-fouling light as function of one or more of a feedback signal and a timer. The term control system may refer to an electronic circuit, such as a sensor in a circuit that after reaching a threshold level allows or induces another action, such as switching on or off the light, and/or may refer to a control unit which may include (programmable) software. In an embodiment, the control system includes a (linear) feed back system. The control system may thus be configured to steer the lighting module (especially its anti-fouling light). The term "to control an intensity" may refer to on/off status of the anti-fouling light but may alternatively or additionally also refer to high and low intensity of the anti-fouling light. It may also refer to a stepwise of stepless increase or decrease of the anti-fouling light between a maximum and a minimum (such as no intensity).

The timer may e.g. be a system that triggers the lighting module to provide light during a certain period and to be switched off during another period. Hence, in an embodiment the lighting system is configured to provide anti-fouling light in a pulsed way wherein periods with anti-fouling light are alternated with periods without anti-fouling light. To this end, e.g. a control system in combination with a timer may be applied, to provide anti-fouling light in a pulsed way. The light pulses may include one or more of block (square) pulses, triangular pulses, sawtooth pulses, unipolar sinus like pulses (like e.g. with rectification), etc. The frequency may range from seconds to hours, or even days. Optionally, the pulsed light may include a slow and a fast pulse, e.g. 3 hours on and 3 hours off, wherein during the on-time, pulsed light is provided with a frequency in the range of 0.001-200 Hz, such as 0.01-20 Hz. By using pulsed light, especially with a relative low frequency, such as <0.01 Hz, biofouling may be formed in the dark periods, and during the on-period, the biofouling may efficiently be removed. In this way, less light may be wasted. In an embodiment, the anti-fouling light is provided 0.2-10 minutes every hour. In yet another embodiment, the anti-fouling light is provided 30-300 minutes every (natural) day, i.e. every 24 hours. The on-time and/or the off-time may be variable, e.g. based on the feedback signal.

The control system may also include a sensor. The term "sensor" may also relate to a plurality of sensors. A typical embodiment for the anti-fouling lighting system could especially include the following:

Sensors for one or more of the parameters (see below);
Software to calculate the required amount of power, based on the parameter values and knowledge (e.g. predefined settings) of minimum power settings to prevent fouling;
A control unit to adjust the effective output power; as a whole, or per section of e.g. the hull or another element.

In a specific embodiment, the control system is configured to control the intensity of the anti-fouling light as function of the feedback of a sensor, wherein the sensor is configured to sense one or more of (i) a velocity of a vessel comprising said lighting module, (ii) a relative velocity of flow of water (at a side of the fouling surface), (iii) a water temperature of water (at a side of the fouling surface), (iv) a loading of a vessel comprising said lighting module, (v) a position of the fouling surface relative to a water level of water (at a side of the fouling surface), and (vi) a presence of one or more of a fouling organism and a fouling organism nutrient in water (at a side of the fouling surface).

Hence, in an embodiment the sensor is configured to sense a velocity of a vessel comprising said lighting module. The sensor may be configured to determine this by measuring the speed of the vessel relative to the water or may receive a signal from a control centre of the vessel which signal contains information about the speed. Hence, in a specific embodiment the sensor is configured to sense a relative velocity of flow of water (at a side of the fouling surface). For instance, with a counterflow, a low speed of the vessel relative to the land surface may still be high enough for preventing biofouling. In such instance, the biofouling light may be switched off. However, with a co-flow, a high speed of the vessel relative to the land surface may still be low enough to allow biofouling. In such instance, the biofouling light may be switched on.

In a further embodiment the sensor is configured to sense a water temperature of water (at a side of the fouling surface) of said optical medium. It is known that in (ant)arctic waters, biofouling may be substantially zero, whereas in tropical waters the biofouling can be very quick. The control system may switch on and off the lighting module dependent upon the temperature, sensed by the sensor.

In yet a further embodiment, the sensor is configured to sense a loading of a vessel comprising said lighting module. This may be simple measurement wherein a sensor in the element or the lighting module senses whether water is in front of the sensor. Is the sensor submerged, the the lighting module may be switched on due to the collaboration between the control system and the sensor. Is the sensor not submerged, the lighting module may be switched off. Hence, in a specific embodiment the sensor is configured to sense a position of the fouling surface relative to a water level of water (at a side of the fouling surface). However, in another embodiment the sensor may receive a signal from a control centre of the vessel which signal contains information about the loading of the vessel. Hence, the sensor may be configured to sense directly or indirectly a loading of a vessel comprising said lighting module.

In yet a further embodiment, the sensor is configured to sense a presence of one or more of a fouling organism and a fouling organism nutrient in water (at a side of the fouling surface). When a level reaches a certain threshold, then the control system may switch on the anti-fouling light; when the threshold is not reached, the control system may switch off the anti-fouling light. For instance, such sensor may be configured to sense one or more of bacteria, sugar, and other nutrients for bioufouling generating species. Hence, the term "presence" may also include concentration. Such sensor may e.g. include a $CO_2$ sensor, a (dissolved) 02 sensor, a BOD sensor, or another type of bioloading sensor, etc. Further, additionally or alternatively, the sensor may include a sensor configured to sense the presence of a fouling organism at the fouling surface, such as in embodiments an emission surface. Such sensor may include an optical sensor, such as a sensor configured to measure one or more of radiation absorption, radiation reflection, radiation transmission, and radiation emission. Here, the term "radiation" especially refers to one or more of UV radiation, visible light and IR radiation, especially one or more of UV radiation and visible light.

The above sensors are described relative to a use in a vessel in water. However, the sensors may be applied as well in other applications and/or other liquids. Further, the sensors are especially described with reference to on/off status. However, optionally or additionally this may relate to high intensity and low intensity anti-fouling light. Further, the sensor is each time described to have a single function. However, a single sensor may in embodiments include different sensors. Further, especially a plurality of sensors may be used, which may be able to sense the same property at different locations and/or may sense a plurality of properties.

The anti-fouling lighting system may comprise a plurality of light sources. For instance, the lighting module may comprise a plurality of light sources. Alternatively or additionally, the anti-fouling lighting system may comprise a plurality of lighting modules. AIs in this embodiment the anti-fouling lighting system may comprise a plurality of light sources. Hence, the anti-fouling lighting system or the lighting module, respectively, may comprise two or more subsets, which subsets may be controlled independently.

As indicated above, the control system is especially configured to control an intensity of the anti-fouling light as function of one or more of (i) a feedback signal related to a biofouling risk and (ii) a timer for time-based varying the intensity of the anti-fouling light. However, alternatively, or additionally, the control system is configured to control an intensity of the anti-fouling light of a first light source in dependence of the intensity of the anti-fouling light of another light source. Hence, in an embodiment the anti-fouling lighting system comprises a plurality of light sources, and the control system is configured to control an intensity of the anti-fouling light of a first light source in dependence of the intensity of the anti-fouling light of another light source. In yet a further embodiment, the lighting module comprises a plurality of light sources, and the control system is configured to control an intensity of the anti-fouling light of a first light source in dependence of the intensity of the anti-fouling light of another light source.

Hence, in an embodiment the control system is configured to control an intensity of the anti-fouling light as function of (i) a feedback signal related to a biofouling risk, and optionally one or more of (ii) a timer for time-based varying the intensity of the anti-fouling light, and (iii) (an)other parameter(s) defined herein.

Yet in another embodiment, the control system configured to control an intensity of the anti-fouling light as function of one or more of (i) a timer for time-based varying the intensity of the anti-fouling light, and optionally one or more of (ii) a feedback signal related to a biofouling risk, and (iii) (an)other parameter(s) defined herein.

Yet in another embodiment, the control system configured to control an intensity of the anti-fouling light as function of a parameter(s) defined herein other than one or more of (i) a feedback signal related to a biofouling risk, and (ii) a timer for time-based varying the intensity of the anti-fouling light; however, optionally in combination with one or more of (i) a feedback signal related to a biofouling risk, and (ii) a timer for time-based varying the intensity of the anti-fouling light.

Hence, in an embodiment the object as defined herein comprises a plurality of lighting modules arranged (in an array) over at least part of a height (h) of the object, wherein the control system is configured to control an intensity of the anti-fouling light as function of a position of the fouling surfaces relative to a water level of water at a side of the system surface. For instance, a vessel may be provided, comprising a plurality of lighting modules arranged (in an array) over at least part of a height (h) of the hull, wherein the control system is configured to control an intensity of the anti-fouling light as function of a position of one or more of the first element surfaces and the emission surfaces relative to a water level of water at a side of the first element surfaces. Especially, the height of the object is defined as the height of the object in use, in e.g. water, from the lowest point below the liquid level to the highest point of the object. Height of elements of such object are defined with the height defined relative to a vertical direction from the lowest point to the highest point. For instance, the height of a hull may be the height from the keel to the e.g. the railing. Advantageously, undesired anti-fouling light above the water level may be reduced (and waste of light and energy may be reduced), whereas below the water level the anti-fouling light may be provided. This also enhances (human (and/or animal) safety, as exposure from e.g. human beings to UV radiation is desirably as low as possible.

Further, the above embodiments including a sensor do not exclude the combination with a timer. For instance, the timer in combination with the control system may reduce the intensity of the anti-fouling light during the night and may increase the intensity during the day.

Again, the same embodiments as described in relation to a vessel may apply to such application in a movable construction in water.

In yet a further aspect, the invention provides a method of anti-fouling a fouling surface of an object that is during use at least temporarily exposed to water or another liquid (that may cause biofouling), the method comprising: (a) providing a lighting module as defined herein; (b) generating the anti-fouling light as function of one or more of (i) a feedback signal related to biofouling risk and (ii) a timer for time-based varying the intensity of the anti-fouling light; and (c) providing said anti-fouling light to said fouling surface.

In a specific embodiment, the invention also provides a method of anti-fouling an element that (during use) is at least partly submerged in a liquid, wherein the element comprises a first element surface (and a second face), the first element surface especially comprising an area of at least 0.4 $m^2$, the method comprising: (a) providing a lighting module comprising (i) a light source configured to generate an anti-fouling light and (ii) an optical medium configured to receive at least part of the anti-fouling light and configured to distribute at least part of the anti-fouling light through the optical medium, the optical medium comprising (iia) a first medium face, especially having an area of at least 0.4 m², the first medium face of the optical medium directed to the first element surface of the element, and (iib) an emission surface configured to emit at least part of the distributed anti-fouling light in a direction away from the first medium face of the optical medium, wherein in a specific embodiment at least part of the lighting module is configured to seal at least part of the first element surface with the emission surface configured more remote from the first element surface than the first medium face; and (b) generating the anti-fouling light as function of one or more of a feedback signal and a timer. In such embodiment, the fouling surface may comprise the emission surface, e.g. when the optical medium is sealing the first element surface. Optionally and additionally, further anti-fouling light may be provided to another surface to be protected (not being the emissive surface).

The phrase "method of anti-fouling" indicates that fouling is prevented and/or fouling may be removed. Hence, the method may be curative and/or preventive. The method may especially further comprise controlling the intensity of the anti-fouling light as function of the feedback of a sensor, such as amongst others defined above. For instance, one may imagine a 3 hours off, 5 minutes on scheme (see also other schemes above).

In yet a further aspect, the invention provides a method of providing an anti-fouling lighting system to an object, that during use is at least temporarily exposed to water, the method comprising attaching a lighting module as defined herein to the object (such as an element thereof), with the lighting module configured to provide said anti-fouling light to a fouling surface of one or more of the object and the lighting module attached to the object. Especially, the object is selected from the group consisting of a vessel, a weir, a dam, a stew, a sluice, a fish farming sea cage, and a buoy, etc.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

Figure 1:
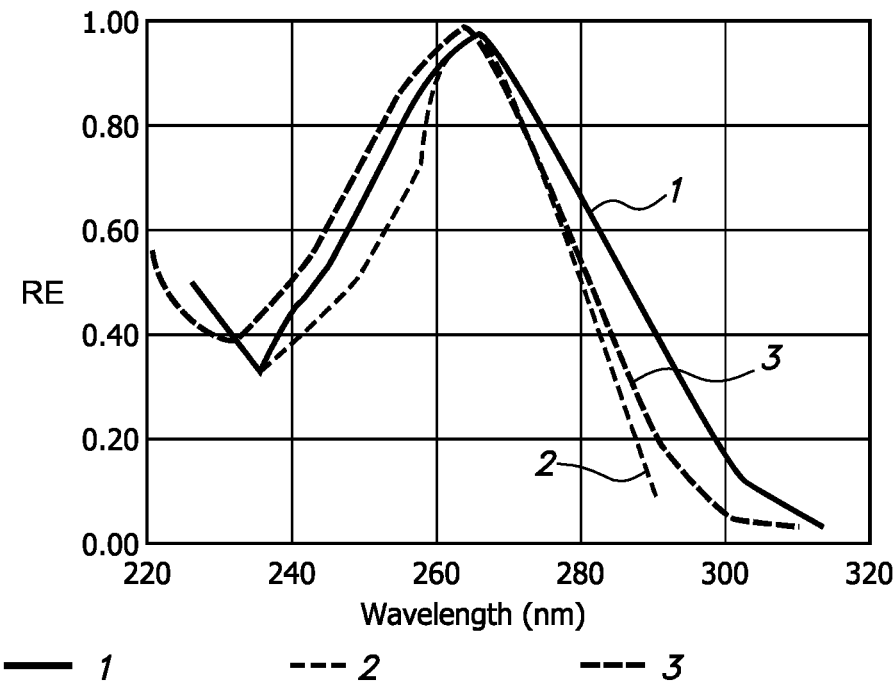
FIG. 1 is a graph showing a germicidal action spectrum for different biological materials as a function of light wavelength.

The drawings are not necessarily on scale.

DETAILED DESCRIPTION OF THE EMBODIMENTS

While the disclosure has been illustrated and described in detail in the drawings and foregoing description, such illustration and description are to be considered illustrative or exemplary and not restrictive; the disclosure is not limited to the disclosed embodiments.

FIG. 1 is a graph showing a germicidal action spectrum for different biological materials as a function of light wavelength, with RE indicating the relative effectiveness, with curve 1 indicating the germicidal action as derived from the IES Lighting Handbook, Application Volume, 1987, 14-19; curve 2 indicating E. Coli light absorption (as derived from W. Harm, Biological Effects of ultraviolet radiation, Cambridge University Press, 1980), and curve 3 indicating DNA absorption (as also derived from the IES handbook).

Figure 2:
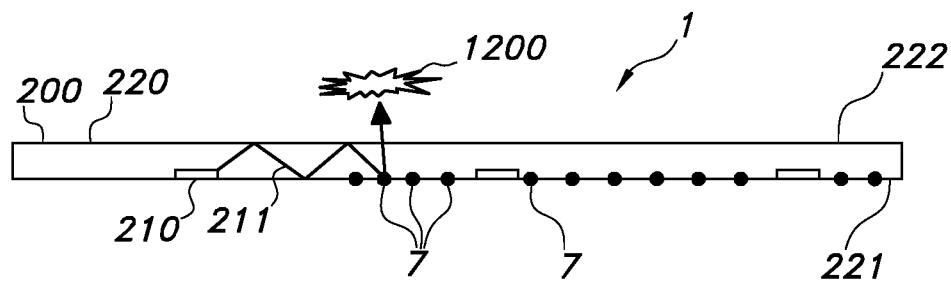
FIG. 2 is a schematic cross section view of a light module with a light guide.

FIG. 2 shows as a basic embodiment a cross section of a lighting module 200 comprising a plurality of light sources 210 (here: side-emitting LEDs, wherein the light is emitted primarily from the side of the LED, and more or less parallel to the surface) encapsulated in a liquid-tight optical medium 220 to guide at least part of the light 211 emitted from the light sources 210 via total internal reflection through the optical medium, which optical medium is further provided with optical structures 7 to scatter light 211 and guided the light 211 out of the optical medium 220 towards an object 1200 to be targeted with the light (a biofouling organism). The optical medium 220 generally extends in two dimensions significantly further than in the third dimension so that a two-dimensional-like object is provided. Optical structures 7 to scatter light 211 may be spread in one or more portions of the optical medium material, possibly throughout all of it, wherein in such portions the distribion may be generally homogeneous or localised. Scattering centres with different structural properties may be combined to provide, besides optical, also structural characteristics, such as resistance to wear and/or impact. Suitable scatterers comprise opaque objects but largely translucent objects may be used as well, e.g. small air bubbles, glass and/or silica; a requirement is merely that a change in refractive index occurs for the wavelength(s) used. Reference 222 indicates an emission surface.

The principle of light guiding and spreading light over a surface is well-known and widely applied in various fields. Here, the principle is applied to UV light for the purpose of anti-fouling. It is noted that the idea of making a surface, e.g. the hull of a ship self-lit with UV is a clearly different solution than the current and well established anti-fouling solutions which rely on smooth coatings, chemicals, cleaning, software to control the ship speed, etc.

Total internal reflection is one way of transmitting light through an optical medium, which is then often referred to as a light guide. To maintain the conditions for total internal reflection, the index of refraction of the light guide should be higher than that of the surrounding medium. However, the use of (partly) reflecting coatings on the light guide and/or use of the reflective properties of the protected surface, e.g. the hull of a ship, itself can also be used to establish the conditions for guiding the light through the optical medium.

In some embodiments the optical medium may be positioned relative to the protected surface, e.g. the hull of a ship, such that a small air gap is introduced between the optical medium and the protected surface; UV light may travel even better—with less absorption—in air than in an optical medium, even when this optical medium is designed as a light guiding material. In other embodiments gas-filled channels, e.g. air channels, may be formed within silicone material. An array of separate gas-filled pockets may also be provided, e.g. in a regular pattern like a rectangular or honeycomb-pattern or in an irregular pattern. Instead of gas (e.g. air) filling, channels and/or pockets may be at least partly filled with a UV-transmissive liquid, e.g. fresh and/or purified water. In case a protected surface that is covered with such optical medium is subject to impact, e.g. a ship hitting a dockside, small pockets may soften, redistribute the impact energy and hence protect the surface, wherein liquid-filled pockets may be robuster under deformation than air-pockets which may more easily burst open.

As most materials have a (very) limited transmittance for UV light, care has to be taken in the design of the optical medium. A number of specific features and/or embodiments, which are dedicated for this purpose are listed in the following:

A relatively fine pitch of low power LEDs can be chosen, to minimize the distance light has to travel through the optical medium.

A 'hollow' structure can be used, e.g. a silicone rubber mat with spacers that keep it a small distance away from the protected surface. This creates air 'channels', through which the UV light can propagate with high efficiency (air is very transparent for UV). Use of gas filled channels provided by such structures allows distributing the UV light over significant distances in a optical medium of material that would otherwise absorb the UV light too strongly to be useful for anti-fouling. Similarly, separate pockets may be formed.

A special material can be chosen with high UV transparency, like certain silicones or UV grade (fused) silica. In embodiments, this special material can be used only for creating channels for the light to propagate the majority of the distance; a cheaper/more sturdy material can be used for the rest of the surface.

Further embodiments are disclosed in the accompanying drawings, wherein a main issue is to illuminate a large surface with anti-fouling light, preferably UV light, yet using point light sources. A typical concern is spreading of the light from point sources to surface illumination. In more detail:

The protected surface area of a typical container ship is 10.000 $m^2$.

A typical LED source has an area of ~1 $mm^2$. This is $10^{10}$ smaller.

Taking the required power levels into account, about 10 LEDs per $m^2$ may be required This means light has to be spread from 1 LED over ~1000 $cm^2$ As another boundary condition is taken that the solution should be thin (order of magnitude: 1 cm), e.g. for reasons such as:

To be able to add the solution as a 'coating' to a ship

To not increase drag due to an increased cross section size of the ship

To keep (bulk) material costs limited.

The use of an optical medium, in particular a generally planar light guide is therefore provided. Typical dimensions of a light guide are a thickness of about 1 mm to about 10 mm. In the other directions, there is no real limit to the size, from an optical point of view; in particular not if plural light sources are provided so that decay of light intensity throughout the light guide due to partial outcoupling of light and possibly (absorption) losses are countered.

Here, it is considered that similar optical challenges apply as with the design of LCD TV backlights, although emission light intensity uniformity is less stringent in anti-fouling than with LCD TV backlights.

Additional ideas and solutions exist to obtain a better uniformity in a thinner optical structure, such as introduction of scatters and/or reflectors or other light spreaders directly in front of one or more light sources.

Figure 3:
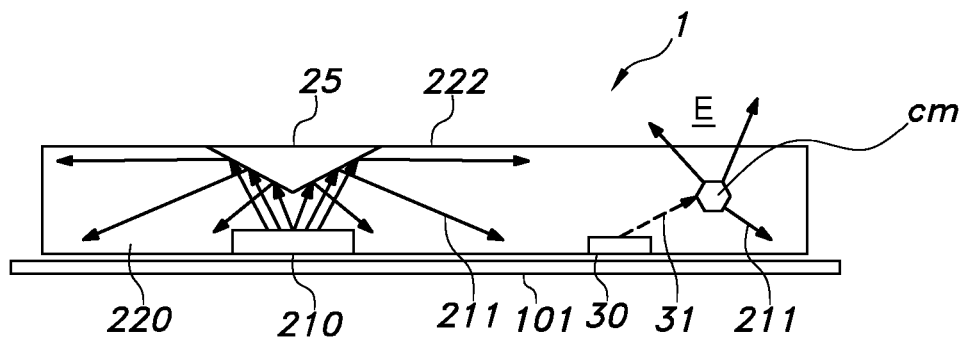
FIG. 3 shows an embodiment comprising a redistribution reflector and a wavelength conversion material.

FIG. 3 shows (left hand side) inclusion of a light spreader in the form of a reflective cone 25 in the optical medium 220 with an apex towards the light source 210. This directs the light 211 in a direction having a component substantially parallel to the surface 101 to be protected against fouling. If the cone 25 is not fully reflective nor opaque, some light from the light source will pass through it and creation of shadows leading to reduced or ineffective anti-fouling is prevented.

Further, FIG. 3 shows a wavelength conversion material CM which is comprised in the optical medium 220. The illustrated embodiment is configured to generate at least part of the anti-fouling light by photo-exciting the wavelength conversion material CM with light from a light source 210 with light 31 having a first wavelength causing the wavelength conversion material to emit anti-fouling light 211 at another wavelength from the optical medium 220 into the environment E, i.e. downstream from the emission surface 222. The distribution of wavelength conversion material in optical medium 220 may be spatially varying, e.g. in accordance with (expected) intensity distributions of (different wavelengths of) light in the optical medium 220. The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

Figure 4A:
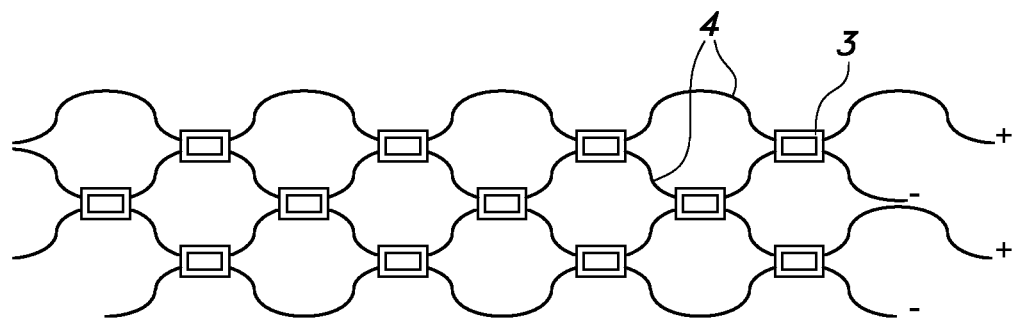
FIGS. 4a-c show embodiments of a chicken-wire grid.
Figure 4B:
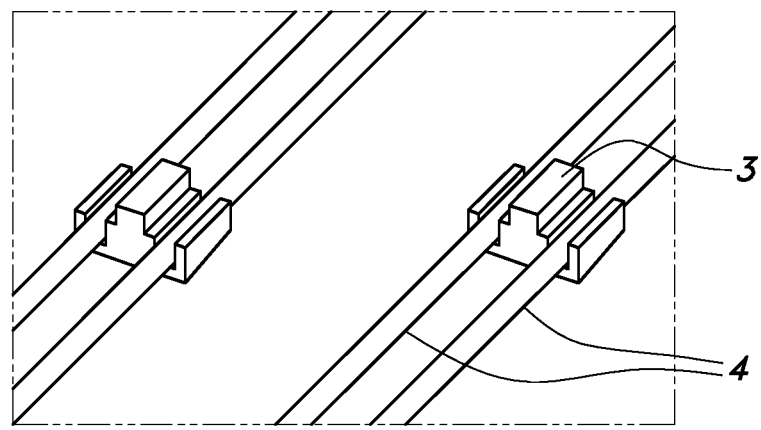
Figure 4C:
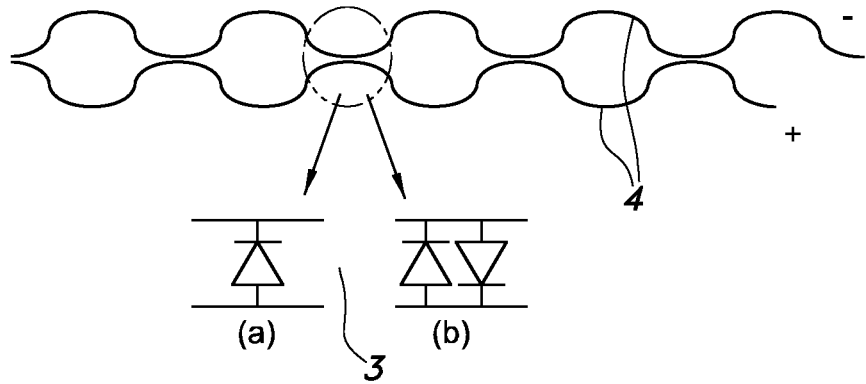

FIGS. 4a-4c shows a chicken-wire embodiment where light sources 210 (here indicated with references 3), such as UV LEDs, are arranged in a grid and connected in a series of parallel connections. The LEDs can be mounted at the nodes as shown in FIG. 4b either through soldering, gluing or any other known electrical connection technique for connecting the LEDs to the chicken wires 4. One or more LEDs can be placed at each node. DC or AC driving can be implemented. In case of DC, the LEDs are mounted as shown in FIG. 4c. If AC is used, then a couple of LEDs in anti parallel configuration is used as shown in FIG. 4c. The person skilled in the art knows that at each node more than one couple of LEDs in anti parallel configuration can be used. The actual size of the chicken-wire grid and the distance between UV LEDs in the grid can be adjusted by stretching the harmonica structure. The chicken-wire grid may be embed in an optical medium wherein optionally a parallel grid of scattering features are provided as illustrated in FIG. 3.

Besides anti-fouling application of hulls of ships, the following alternative applications and embodiments are envisioned:

The disclosure can be applied to a wide variety of fields. Almost any object coming into contact with natural water, will over time be subject to biofouling. This can hinder e.g. water inlets of desalination plants, block pipes of pumping stations, or even cover the walls and bottom of an outdoor pool. All of these applications would benefit from the presently provided method, lighting modules and/or system, i.e. an effective thin additional surface layer, which prevents biofouling on the entire surface area.

Although UV light is the preferred solution, other wavelengths are envisaged as well. Non-UV light (visible light) is also effective against biofouling. Typical micro-organisms are less sensitive to non-UV light than to UV light, but a much higher dose can be generated in the visible spectrum per unit input power to the light sources.

UV LEDs are an ideal source for thin light emitting surfaces. However, UV sources other than LEDs can also be used, such as low pressure mercury vapour lamps. The form factor of these light sources are quite different; mainly the source is much bigger. This results in different optical designs, to 'distribute' all the light from a single source over a large area. The concept of light guiding as discussed herein does not change though. Further, a significant contribution of light in desired wavelengths and/or wavelength combinations may be produced.

Instead of using a thin layer that emits UV light outward in a direction away from the protected surface in order to avoid bio-fouling, biofouling could potentially also be removed by applying UV light from the outside in the direction of the protected surface. E.g. shining a UV light onto a hull or surface comprising a suitable optical medium as described. Thus, a single optical medium emitting anti-fouling light in directions to and away from protected surfaces may be even more efficient.

Figure 5A:
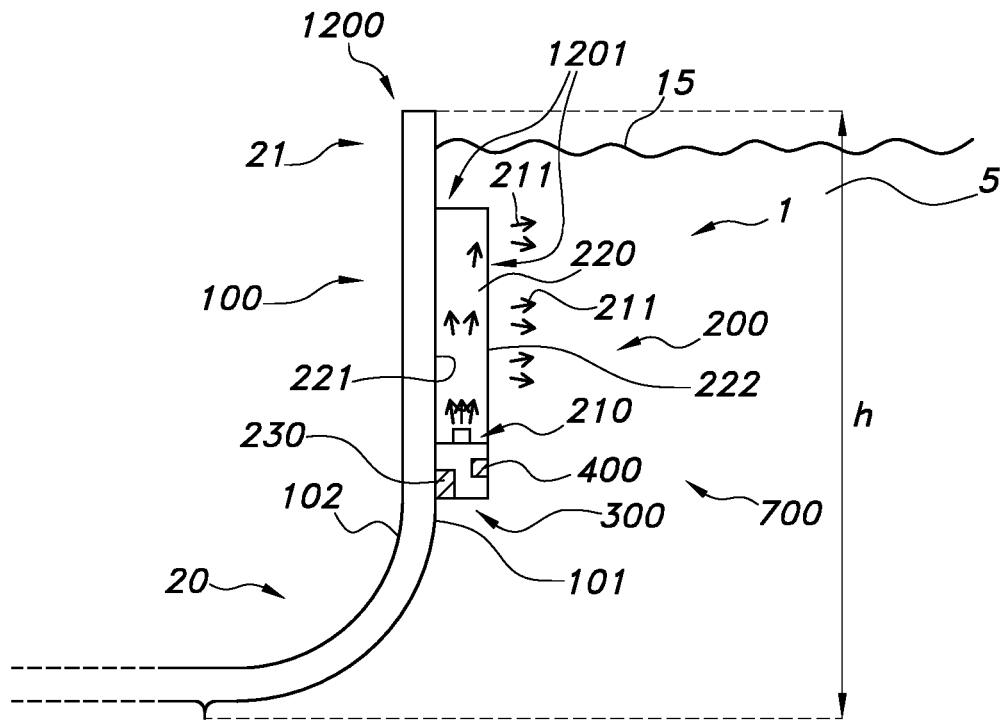
FIGS. 5a-5d schematically depict some aspect of the lighting system as described herein.

FIGS. 5a-5d schematically depict some embodiments and variations of the anti-fouling system. FIG. 5a schematically depicts an anti-fouling lighting system 1 comprising an element 100, such as e.g. a hull 21, a lighting module 200, and a control system 300. Here, as example of an object 1200 with fouling surface 1201, a vessel 20 with said hull 21 is schematically depicted. The fouling surface 1201 may be (part of) an element 100 and/or the surface of an element or system associated with said object 1200. Element 100 indicates an element of the object, such as e.g. a hull 21 of a vessel 20. In this schematically depicted embodiment, the object 1200 further comprises the anti-fouling lighting system that includes an emissive surface (see below). Hence, the fouling surface may e.g. also comprise such emissive surface.

The element 100 comprises a first element surface 101 (and a second face 102), the first element surface 101 comprising e.g. an area of at least 0.4 m². For instance, the second face 102 can be the internal wall of the hull 21 of a vessel 20. The first element surface 101 is the face towards the exterior of, in this embodiment the vessel 20, which will during use at least partly be in contact with liquid 5, especially water. The liquid level is indicated with reference 15. As can be seen, at least part of the element 100 is submerged.

The lighting module 200 comprises a light source and an optical medium 220. Especially, the light source 210 is configured to generate anti-fouling light 211, which may especially include UV light, even more especially at least UV-C light. The optical medium 220 is especially configured to receive at least part of the anti-fouling light 211 and is further configured to distribute at least part of the anti-fouling light 211 through the optical medium 220. The optical medium comprises a first medium face 221, which may for instance have an area of at least 0.4 m² and an emission surface 222 configured to emit at least part of the distributed anti-fouling light 211 in a direction away from the first medium face 221 of the optical medium 220. Here, the first medium face 221 is directed to the first element surface 101 of the element 100. In this embodiment, the optical medium 220 is in physical contact to the first element surface 101 of the optical element. For instance, in such embodiment at least part of the lighting module 200 is thus configured to seal at least part of the first element surface 101 with the emission surface 222 configured more remote from the first element surface 101 than the first medium face 221. Further, the lighting system 1 comprises a control system 300 configured to control an intensity of the anti-fouling light 211 as function of one or more of a feedback signal and a timer. The optional timer is not depicted, but may optionally be integrated in the control system. Alternatively, a sensor, indicated with reference 400, may sense a time signal. Reference 230 indicates a power supply, which may locally harvest energy, or which may e.g. be a battery.

Optionally, electrical power may be provided from the vessel. Reference h indicates the height of the element 100.

Figure 5B:
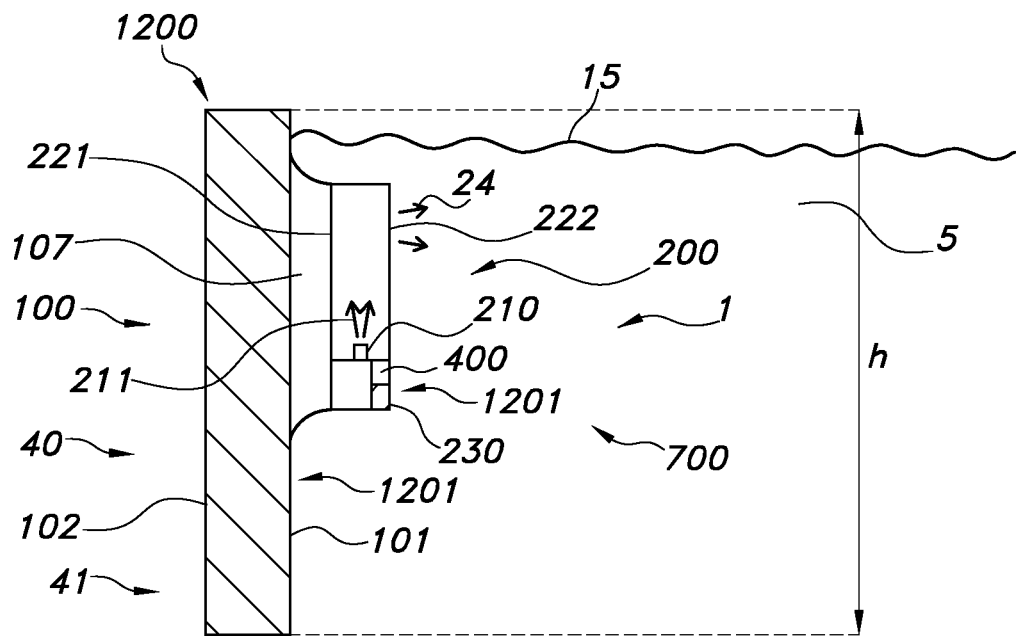
Figure 5C:
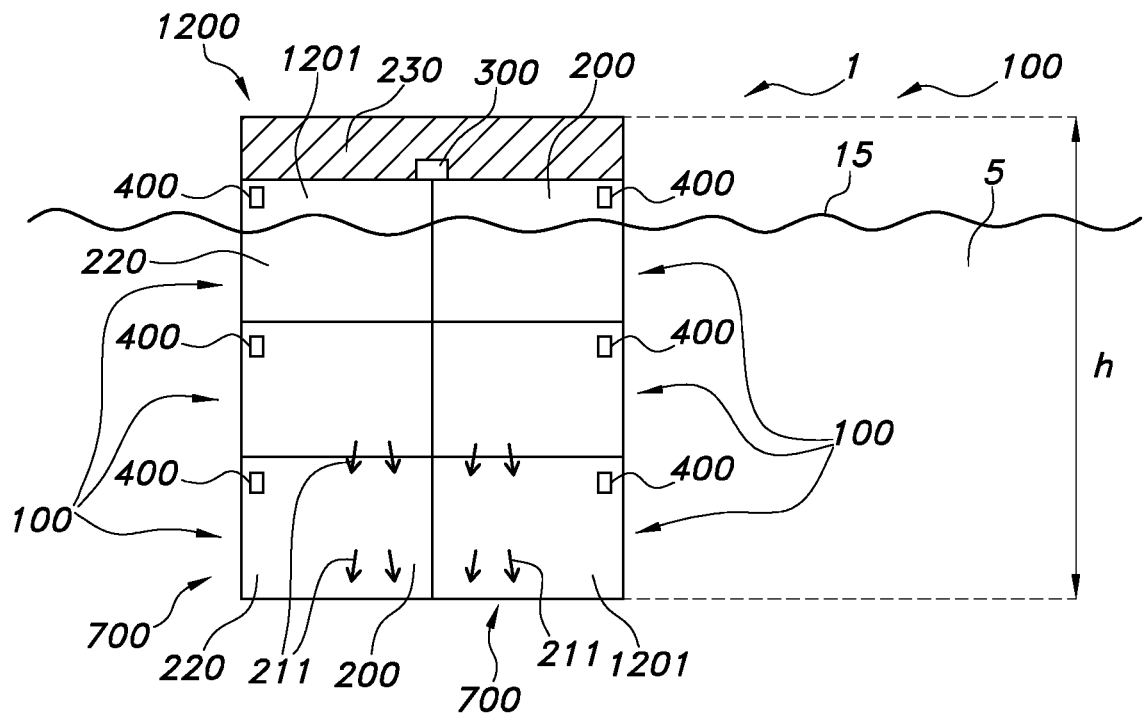
Figure 5D:
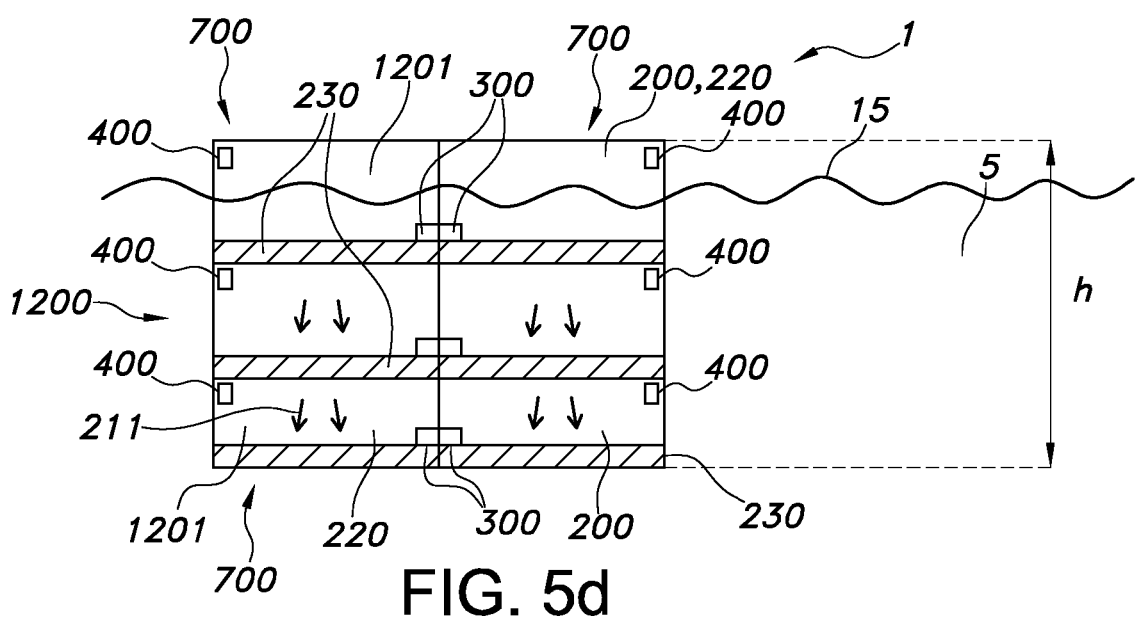

By way of example, the power supply 230, control system 300, and sensor 400 are all integrated in the lighting module 200, and form with the optical medium 220 a single unit. The lighting module 200 may substantially cover the entire element 100. Here, by way of example, only part of the 1$^{st}$ face 101 is covered. In the embodiment depicted in FIG. 5a, the 1$^{st}$ optical medium surface is attached to the 1$^{st}$ face of the element 100. FIG. 5b schematically depicts an embodiment, just by way of example, wherein the optical medium is not attached to the element 100; hereby a void 107 may be created. Note that at least part of the lighting unit seals the first element surface of the element 100. Here, by way of example the element is a wall or door or a moveable construction 40, e.g. a dam or sluice. FIG. 5c by way of examples shows a plurality of elements 100, and also a plurality lighting modules 200. The lighting system includes also a plurality of sensors 400, and a single control system 300. Further, the local energy harvesting system 230 may e.g. a photovoltaic cell. The lighting modules 200 may in an embodiment form a single integrated unit, and seal of as a whole the elements 100. With such system, it may be monitored which optical mediums 220 are below the liquid level 15. Only those which are below the liquid level 15 may provide anti-fouling light 211, as indicated in the drawing. Of course, more than the schematically depicted lighting modules may be available. FIG. 5d schematically depicts individual lighting system 1, which may optionally also be coupled. E.g., the control systems 300 may optionally communicate (wireless). However, the lighting systems may also act independently.

The sensor 400 may e.g. be configured to sense one or more of (i) a velocity of a vessel comprising said lighting module 20), (ii) a relative velocity of flow of water, (iii) a water temperature, (iv) a loading of a vessel comprising said lighting module 220, (v) a position of the fouling surface 1201 relative to a water level of water, and (vi) a presence of one or more of a fouling organism and a fouling organism nutrient in water. For instance, the sensor may comprise a dissolved oxygen sensor and/or a water level sensor. Also combinations of two or more different types of sensors may be applied and/or same type of sensors at different heights may be applied. Note that the fouling surface 1201 may in some of the embodiments (also) comprise the emission surface (222), see amongst others FIGS. 5a-5b.

The embodiments schematically depicted in FIGS. 5a-5d show lighting modules 200 that may at least partly seal a surface. However, also other embodiments may be applied, e.g. optical media, such as a fiber or a waveguide directing light to the fouling surface 1201.

The integrated unit 700, as for instance shown in some of the schematically depicted embodiments, may especially be a closed unit, with the emissive surface 221 as one of the faces.

With respect to for instance FIGS. 5c-5d, the anti-fouling lighting system may include a plurality of light sources (not depicted but included in the lighting modules). The control unit may control light sources e.g. as function of the intensity needed. For instance, rather than having all light sources turned on, and turned off, at the same time, it may also be possible to have nearby/neighboring light sources flash in counterphase. That is, say a light is programmed to be on 50% of the time, the neighbor will be OFF when the first light is ON; and vice versa. The advantage is that e.g. the same amount of energy is saved (50%), but a better effect may be achieved in certain places (i.e. halfway between the two lights, a fouling organism will now receive a continuous dose, rather than having a "recovery time" in between light dosis). Hence, the anti-fouling lighting system (or lighting module) comprises a plurality of light sources, and the control system 300 is configured to control an intensity of the anti-fouling light 211 of a first light source in dependence of the intensity of the anti-fouling light 211 of another light source 210. When using a plurality of modules, this may also imply in embodiments that the control system 300 is configured to control an intensity of the anti-fouling light 211 of a first lighting module in dependence of the intensity of the anti-fouling light 211 of another lighting module.

The concepts are not restricted to the above described embodiments which can be varied in a number of ways within the scope of the claims. For instance, using light, in particular UV light as an anti-biofouling means can provide an interesting opportunity in other fields. It is unique in the sense that continuous "24/7" 'protection' can be provided, over a large area. The application is especially interesting for the hull of ships, but can also be applied in swimming pools, water treatment plants, etc. Instead of water, biofouling may occur and be treated in other liquid environments, e.g. oils, brines and/or liquids in other environments including food industry. Hence, the invention is especially explained in relation to water, such as seawater. However, the invention is not limited to such applications only. Hence, in embodiments, the term "water" may be replaced by liquid. Especially, such liquid may also include biofouling species an nutrients for such bioufouling species.

Elements and aspects discussed for or in relation with a particular embodiment may be suitably combined with elements and aspects of other embodiments, unless explicitly stated otherwise.

Hence, anti-fouling solutions that release certain chemicals or biocides currently have a large market share. To be effective, these coatings have to provide an environment which is harsh for living creatures. A drawback is that over time—either by intended release, or by the inevitable cleaning of the surface—those chemicals are released into the water. These chemicals quite often remain active, causing adverse effects on the environment. A fundamentally different way of preventing bio-fouling is by using UV light emission. UV light is known to be effective in de-activating or even killing micro-organisms, provided a sufficient dose of a suitable wavelength is applied. An example of such is ballast-water treatment. We present a new approach for anti-biofouling, in which an UV-light emitting layer is applied on the outside of the hull of a ship. The introduction of UV-LEDs as a light source enables thin, coating like structures, in which the UV light is spread evenly within the surface. Further optical design elements will ensure the light escapes more or less uniformly all over the coating layer. The UV emitting layer will make it reduce the possibility for micro-organisms to attach to the hull or even prevent it.

In an experimental setup, we have achieved promising results in keeping a surface free from bio-fouling for an extended period of time. Two elements were arranged in seawater and kept there for four weeks. One was irradiated with UV light; the other was not irradiated with UV light. After four weeks, the former included only fouling at the spot where no UV light was received; the spot itself was free from fouling. The latter element was fully covered with fouling.

The invention claimed is:

1. An anti-fouling membrane that is configured to provide anti-fouling protection to a protected surface, comprising:

a first surface that is configured to face the protected surface, a second surface, opposite the first surface that is configured to emit UV radiation from the membrane in a direction from the first surface to the second surface, an optical medium between the first surface and the second surface, wherein the optical medium comprises:
- a plurality of UV light emitters configured to emit the UV radiation,
- a silicone material that is embedded with other particles between the first surface and the second surface,
  - wherein a density of the other particles in the silicone increases from within the optical medium towards the second surface.

2. The anti-fouling membrane of claim 1, wherein the other particles comprise particles of silica.

3. The anti-fouling membrane of claim 1, wherein the other particles comprise particles of at least one of: silica, glass, and mica.

4. The anti-fouling membrane of claim 1, wherein the other particles comprise particles that are selected from the group of: translucent particles, opaque particles, and optically active particles.

5. The anti-fouling membrane of claim 1, wherein the other particles comprise flakes.

6. The anti-fouling membrane of claim 1, wherein the silicone material comprises layers of silicone, wherein the density of other particles is higher in the layers of silicone that are closer to the second surface.

7. The anti-fouling membrane of claim 6, wherein the other particles comprise flakes, and an orientation of the flakes is generally parallel to a direction of expansion of the protected surface.

8. The anti-fouling membrane of claim 1, wherein the first and second surfaces comprise silicone.

9. The anti-fouling membrane of claim 1, wherein the density of the other particles varies between 0% adjacent to the first surface and 95% adjacent to the second surface.

10. The anti-fouling membrane of claim 1, further comprising spacers situated on the first surface that create a plurality of voids between the first surface and the protected surface.

11. The anti-fouling membrane of claim 10, wherein the voids are filled with gas that is more transparent to the UV radiation than the optical medium.

12. An anti-fouling membrane that is configured to provide anti-fouling protection to a protected surface, comprising:
- a first surface that is configured to be situated adjacent to the protected surface,
- a second surface, opposite the first surface that is configured to emit UV radiation from the membrane,
- an optical medium between the first surface and the second surface,
- wherein the optical medium comprises:
  - a plurality of light emitters configured to emit radiation at a first wavelength,
  - a plurality of wavelength conversion particles that convert radiation at the first wavelength to the UV radiation that is emitted from the second surface.

13. The antifouling membrane of claim 12, wherein a density of the wavelength conversion particles varies based on a spatial arrangement of the light emitters.

14. A method of producing an anti-fouling membrane that is configured to provide anti-fouling protection to a protected surface, comprising:
- forming a first layer having a first surface and an interior surface, wherein the first surface is configured to face the protected surface,
- situating a plurality of light emitters and corresponding conductive elements for providing energy to the light emitters on the interior surface,
- applying an optical medium upon the interior surface and the light emitters, wherein the optical medium provides a second surface, opposite the first surface, through which anti-fouling radiation created by the light emitters is emitted from the optical medium,
- wherein the optical medium comprises:
  - a silicone material that is embedded with other particles between the first surface and the second surface,
  - wherein a density of the other particles in the silicone increases from within the optical medium towards the second surface.

15. The method of claim 14, wherein:
the plurality of light emitters are configured to emit radiation at a first wavelength,
wherein the optical medium also comprises a plurality of wavelength conversion particles that convert radiation at the first wavelength to the UV radiation that is emitted from the second surface.

16. The method of claim 14, wherein the plurality of light emitters emit the UV radiation that is emitted from the second surface.

17. The method of claim 14, wherein the other particles comprise particles of silica.

18. The method of claim 14, wherein the other particles comprise particles of at least one of: silica, glass, and mica.

19. The method of claim 14, wherein the other particles comprise particles that are selected from the group of: translucent particles, opaque particles, and optically active particles.

20. The method of claim 14, further comprising situating spacers on the first surface that are configured to create a plurality of voids between the first surface and the protected surface.

* * * * *